US011638775B2

(12) United States Patent
Young et al.

(10) Patent No.: US 11,638,775 B2
(45) Date of Patent: May 2, 2023

(54) HYDROGEL COMPOSITIONS BONDED TO POLYMERIC SUBSTRATES

(71) Applicant: 3M INNOVATIVE PROPERTIES COMPANY, St. Paul, MN (US)

(72) Inventors: Alexi J. Young, Shoreview, MN (US); Jerald K. Rasmussen, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 487 days.

(21) Appl. No.: 15/753,196

(22) PCT Filed: Sep. 26, 2016

(86) PCT No.: PCT/US2016/053668
§ 371 (c)(1),
(2) Date: Feb. 16, 2018

(87) PCT Pub. No.: WO2017/058698
PCT Pub. Date: Apr. 6, 2017

(65) Prior Publication Data
US 2018/0236124 A1  Aug. 23, 2018

Related U.S. Application Data

(60) Provisional application No. 62/234,784, filed on Sep. 30, 2015.

(51) Int. Cl.
| | | |
|---|---|---|
| *C08J 7/06* | (2006.01) | |
| *C08J 3/075* | (2006.01) | |
| *C09D 4/00* | (2006.01) | |
| *A61L 15/60* | (2006.01) | |
| *C08L 33/10* | (2006.01) | |
| *C08L 33/26* | (2006.01) | |
| *C08F 220/54* | (2006.01) | |
| *C08J 7/04* | (2020.01) | |
| *C08J 7/043* | (2020.01) | |
| *C08J 7/056* | (2020.01) | |

(52) U.S. Cl.
CPC ............ *A61L 15/60* (2013.01); *C08F 220/54* (2013.01); *C08J 7/043* (2020.01); *C08J 7/0427* (2020.01); *C08J 7/056* (2020.01); *C08L 33/10* (2013.01); *C08L 33/26* (2013.01); *C09D 4/00* (2013.01); *C08J 2375/04* (2013.01); *C08J 2400/14* (2013.01); *C08J 2433/06* (2013.01); *C08J 2433/26* (2013.01)

(58) Field of Classification Search
None
See application file for complete search history.

(56) References Cited

U.S. PATENT DOCUMENTS

| | | |
|---|---|---|
| 5,209,849 A | 5/1993 | Hu |
| 5,776,611 A | 7/1998 | Elton |
| 6,710,104 B2 | 3/2004 | Haraguchi |
| 7,696,259 B2 | 4/2010 | Hanley |
| 7,993,892 B2 | 8/2011 | Takada |
| 8,513,320 B2 | 8/2013 | Rooijmans |
| 8,530,564 B2 | 9/2013 | Takada |
| 8,809,411 B2 | 8/2014 | Rooijmans |
| 8,957,125 B2 | 2/2015 | Belt |
| 2002/0128618 A1 | 9/2002 | Frenz |
| 2006/0148352 A1 | 7/2006 | Munro |
| 2009/0155575 A1 | 6/2009 | Dias |
| 2009/0291500 A1* | 11/2009 | Takada .................. C08F 220/54 |
| | | 435/396 |
| 2010/0119833 A1 | 5/2010 | Madsen |
| 2010/0198168 A1* | 8/2010 | Rooijmans ............... C09D 5/00 |
| | | 604/265 |
| 2011/0059874 A1 | 3/2011 | Rooijmans |

FOREIGN PATENT DOCUMENTS

| | | |
|---|---|---|
| GB | 2464080 | 4/2010 |
| JP | 47-40913 | 10/1972 |
| JP | 2007-126572 | 5/2007 |
| JP | 2007117275 | 5/2007 |
| JP | 2015003973 | 1/2015 |
| WO | WO 2008-104572 | 9/2008 |

(Continued)

OTHER PUBLICATIONS

Allen, "Photochemistry of Novel Water-Soluble Para-Substituted Benzophenone Photoinitiators: A Polymerization, Spectroscopic and Flash Photolysis Study," Journal of Photochemistry and Photobiology, A.: Chemistry, 1988, vol. 44, pp. 349-360.

Drtina, "Highly Cross-Linked Azlactone Functional Supports of Tailorable Polarity", Macromolecules, 1996, vol. 29, 4486-4489.

Guttierez-Villarreal, "Surface Graft Polymerization of N-vinylcaprolactam onto Polylactic Acid Film by UV Irradiation", Journal of Polymer Research, 2013, vol. 20, No. 149, pp. 1-6.

Haraguchi, "Compositional Effects on Mechanical Properties of Nanocomposite Hydrogels Composed of Poly(N,N-dimethylacrylamide) and Clay", Macromolecules, 2003, vol. 36, pp. 5732-5741.

Pandiyarajan, "Influence of the Molecular Structure of Surface-Attached Poly(N-alkyl Acrylamide) Coatings on the Interaction of Surfaces with Proteins, Cells, and Blood Platelets", Macromolecular Bioscience, 2013, vol. 13, pp. 873-884.

(Continued)

*Primary Examiner* — Ronak C Patel

(57) ABSTRACT

Described herein is a multilayer article comprising: a. a polymer substrate comprising an abstractable atom; and b. a hydrogel coating thereon wherein the hydrogel coating has a water content of at least 10 wt % and is covalently bonded to the polymer substrate, and wherein the hydrogel coating is derived from an aqueous composition having a pH less than 9.5, the aqueous composition comprising: (a) a hydrophilic monomer selected from at least one of (meth)acrylate or (meth)acrylamide; (b) at least 0.1 wt % of a water-swellable clay; (c) a first initiator, wherein the first initiator is water-soluble and is a Type I photoinitiator; and (d) a second initiator, wherein the initiator is water-soluble and is a Type II photoinitiator; and (e) an acid.

19 Claims, No Drawings

(56) References Cited

FOREIGN PATENT DOCUMENTS

WO    WO 2011-157805      12/2011
WO    WO 2014/118382    *   8/2014

OTHER PUBLICATIONS

Ranby, "Surface Modification and Lamination of Polymers by Photografting", International Journal of Adhesion and Adhesives, 1999, vol. 19, pp. 337-343.

Ranby, "Surface Photografting of Polymer Fibers, Films and Sheets", Nuclear Instruments and Methods in Physics Research B, 1999, vol. 151, pp. 301-305.

Ruckert, "Surface Modification of Polymers-IV. Grafting of Acrylamide via an Unexpected Mechanism using a Water Soluble Photo-Initiator", European Polymer Journal, 1996, vol. 32, No. 2, pp. 201-208.

Tretinnikov, "Benzophenone-Initiated Grafting Photopolymerization of Acrylic Acid on the Surface of Polyethylene from the Monomer Aqueous Solution without its Deaeration", Polymer Science, Series B, 2012, vol. 54, No. 9-10, pp. 427-433.

Yang, "Surface Hydrophilization of Microporous Polypropylene Membrane by Grafting Zwitterionic Polymer for Anti-Biofouling", Journal of Membrane Science, 2010, Vo. 362, pp. 255-264.

International Search Report for PCT International Application No. PCT/US2016/053668, dated Jan. 19, 2017, 4pgs.

* cited by examiner

HYDROGEL COMPOSITIONS BONDED TO POLYMERIC SUBSTRATES

CROSS REFERENCE TO RELATED APPLICATIONS

This application is a national stage filing under 35 U.S.C. 371 of PCT/US2016/053668, filed Sep. 26, 2016, which claims the benefit of U.S. application Ser. No. 62/234784, filed Sep. 30, 2015, the disclosure of which is incorporated by reference in its/their entirety herein.

TECHNICAL FIELD

Hydrogel compositions bonded to polymeric substrates are disclosed.

BACKGROUND

Wounds or lesions typically exude liquid material after formation and during the healing process. When selecting a dressing, a balance needs to be struck between the desire to remove exudate from the wound and maintaining an appropriate level of fluid in and around the wound to prevent it becoming too dry or too wet.

Hydrogels have been increasingly used in wound care because of their ability to absorb water and keep the wound in a suitably moist condition, which promotes healing.

Hydrogels are hydrophilic polymers characterized by their hydrophilicity (i.e., capacity to absorb large amounts of fluid such as wound exudate) and insolubility in water (i.e. they are capable of swelling in water while generally preserving their shape). The hydrophilicity is generally due to groups such as hydroxyl, carboxy, carboxamido, and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of covalent crosslinking, but additionally may result from electrostatic, hydrophobic or dipole-dipole interactions.

Most hydrogels used for wound care are non-adhesive and thus, must be secured into a backing layer with either an adhesive to fixedly attach the hydrogel onto the backing layer and/or through the use of a netting placed between the wound and the hydrogel such as disclosed in U.S. Pat. Publ. No 2006/0148352 (Munro et al.). Adhesive hydrogels can be used, however, once in-contact with the wound exudate or other aqueous solutions, the hydrogel imbibes water. This can reduce the hydrogel's tackiness and thus, diminish or eliminate adhesion between the hydrogel and the backing layer.

SUMMARY

There is a desire for identifying an alternative means of robustly adhering hydrogels onto a polymeric substrate.

In one aspect, a multilayer article is disclosed comprising:
(i) a polymer substrate comprising an abstractable atom; and
(ii) a hydrogel coating thereon wherein the hydrogel coating has a water content of at least 10 wt % and is covalently bonded to the polymer substrate, and wherein the hydrogel coating is derived from an aqueous composition having a pH less than 9.5, the aqueous composition comprising:

(a) a hydrophilic monomer selected from at least one of (meth)acrylate or (meth)acrylamide;
(b) at least 0.1 wt % of a water-swellable clay;
(c) a first initiator, wherein the first initiator is water-soluble and is a Type I photoinitiator; and
(d) a second initiator, wherein the initiator is water-soluble and is a Type II photoinitiator; and
(e) an acid.

In another embodiment, a method of making a hydrogel coated article is described, the method comprising:
(i) providing an aqueous composition having a pH less than 9.5, the aqueous composition comprising:
(a) a hydrophilic monomer selected from at least one of (meth)acrylate or (meth)acrylamide;
(b) at least 0.1 wt % of a water-swellable clay;
(c) a first initiator, wherein the initiator is water-soluble and is a Type I photoinitiator;
(d) a second initiator, wherein the initiator is water-soluble and is a Type II photoinitiator; and
(e) an acid;
(ii) contacting the aqueous composition to a polymer substrate comprising an abstractable atom; and
(iii) curing the aqueous composition.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"interpolymerized" refers to monomers that are polymerized together to form a polymer backbone;

"(meth)acrylate" refers to compounds containing either an acrylate or a methacrylate structure or combinations thereof;

"(meth)acrylamide" refers to compounds containing either an acrylamide or a methacrylamide structure or combinations thereof; and "monomer" is a molecule which can undergo polymerization which then forms part of the essential structure of a polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Hydrogels

A hydrogel is a network of hydrophilic polymer chains, which are dispersed in an aqueous medium. The water-swollen polymeric networks are rendered insoluble due to interactions (e.g., crosslinks) between polymer chains. When this network of hydrophilic polymers is placed in an aqueous solution, these systems often imbibe water until they reach an equilibrium swelling point. At this point, the enthalpy of mixing equals the restrictions imposed by the interactions (e.g., covalent bonding between chains, or noncovalent interactions (H-bonding, electrostatic, van der Waals) between chains) that hold the polymer chains together.

A hydrogel has the capacity to absorb many times (e.g. at least about 2.5, 5, 10, or even 50 times, and potentially up to about 250 times) its own weight of exudate or other fluid (e.g. water) in 24 hours.

Typically, the covalent attachment of hydrogels onto substrates is described with glass substrates, where bonds formed between glass and alkoxysilyl-containing reactive monomers are utilized. Once the alkoxysilyl groups of the monomer have reacted with and formed a bond with the glass substrate, the reactive pendant group on the monomer can be utilized to initiate polymerization of a network hydrogel. This attachment method is dependent on the inherent reactivity of the glass substrate. In the case of polymeric substrates, such as films based on polyolefins, polyurethanes, and polyesters, the substrate surface does not have the required innate reactivity for easy modification. The present disclosure is directed toward a method for the durable attachment (e.g., covalent attachment) of a hydrogel composition onto a polymeric substrate and articles therefrom.

The substrates of the present disclosure are organic polymeric substrates, more specifically a polymeric substrate comprising an abstractable atom, typically, a hydrogen atom.

Exemplary polymeric substrates include polyamides such as nylons, polyesters such as polyethylene terephthalate (PET), polyolefins such as polypropylene, and polyurethanes.

The hydrogel coating of the present disclosure has a water content of at least 10, 15, 20, 30, 40, or even 50 wt %. The hydrogel coating is derived from an aqueous composition comprising a hydrophilic monomer, a water-swellable clay, and two different water-soluble photoinitiators. As will be discussed and shown herein, it has been discovered that by lowering the pH of the aqueous composition, durable attachment of the hydrogel coating onto a polymeric substrate can be achieved. In one embodiment of the present disclosure, the hydrogel coating disclosed herein, after absorbing exudate or other fluids, remains attached to the polymeric substrate.

The hydrophilic monomer is a monomer that is soluble in water and/or is soluble in mixed solution comprising organic solvents miscible with water, having water as the main component. In one embodiment, the monomer has a lipophilicity index less than or equal to 20. As used herein, the term "lipophilicity index" or "LI" refers to an index for characterizing the hydrophobic or hydrophilic character of a monomer. The lipophilicity index is determined by partitioning a monomer in equal volumes (1:1) of a non-polar solvent (e.g., hexane) and a polar solvent (e.g., a 75:25 acetonitrile-water solution). The lipophilicity index is equal to the weight percent of the monomer remaining in the non-polar phase after partitioning. Monomers that are more hydrophobic tend to have a higher lipophilicity index; similarly, monomers that are more hydrophilic tend to have a lower lipophilicity index. Measurement of lipophilicity index is further described in Drtina et al., *Macromolecules*, 29, 4486-4489 (1996). Examples of non-ionic monomers that have a sufficiently low lipophilicity index include, but are not limited to, hydroxyalkyl(meth)acrylates such as 2-hydroxyethylacrylate, 3-hydroxypropylacrylate, 2-hydroxyethylmethacrylate (e.g., LI is 1), and 3-hydroxypropylmethacrylate (e.g., LI is 2); acrylamide (e.g., LI is less than 1) and methacrylamide (LI is less than 1); glycerol monomethacrylate and glycerol monoacrylate; N-alkyl (meth)acrylamides such as N-methylacrylamide (e.g., LI is less than 1), N,N-dimethylacrylamide (e.g., LI is less than 1), N-methylmethacrylamide, and N,N-dimethylmethacrylamide; N-vinylamides such as N-vinylformamide, N-vinylacetamide, and N-vinylpyrrolidone; acetoxyalky(meth) acrylates such as 2-acetoxyethylacrylate and 2-acetoxyethylmethacrylate (e.g., LI is 9); glycidyl(meth) acrylates such as glycidylacrylate and glycidylmethacrylate (e.g., LI is 11); and vinylalkylazlactones such as vinyldimethylazlactone (e.g., LI is 15).

Hydrophilic monomers are known in the art and include vinyl monomers such as (meth)acrylates, and (meth)acrylamides.

Exemplary (meth)acrylate monomers include: acrylic acid (3-sulphopropyl) ester (SPA) and salts thereof, N,N-dimethylaminoethylmethacrylate and salts thereof, [2-(methacryloyloxy)ethyl]dimethyl-(3-sulfopropyl) ammonium hydroxide, [2-(methacryloyloxy)ethyl] trimethylammonium chloride, 2-hydroxyethyl(meth) acrylate, hydroxypropyl(meth)acrylate, and polyethyleneglycolmono(meth)acrylate.

Exemplary (meth)acrylamide monomers include: N-substituted (meth)acrylamide derivatives, such as N-Methylacrylamide, N-ethylacrylamide, cyclopropylacrylamide, N-isopropylacrylamide, N-methylmethacrylamide, cyclopropylmethacrylamide, N-isopropylmethacrylamide, diacetone acrylamide, hydroxyethyl acrylamide, 2-acrylamido-2-methylpropane sulphonic acid (AMPS) and salts thereof and N,N-di-substituted (meth)acrylamide derivatives, such as N,N-dimethylacrylamide, N,N-dimethylaminopropylacrylamide, N-methyl-N-ethylacrylamide, N-methyl-N-isopropylacrylamide, N-methyl-N-n-propylacrylamide, N,N-diethylacrylamide, N-acryloylpyrrolidine, N-acryloylpiperidine, N-acryloyl-N'-methylhomopiperidine, and N-acryloyl-N'-methylpiperidine, N-acryloyl morpholine or a substituted derivative thereof, and N,N dimethylaminopropylmethacrylamide.

Other useful water soluble monomers include vinyl amides such as N-vinylacetamide, N-vinylformamide, N-vinylpyrrolidinone, and vinylpyridine.

In one embodiment, the vinyl monomers are substituted with acid or ionic groups (which may, for example, be salts of acid groups or tertiary ammonium groups). Such salts may include, for example, sodium, potassium, lithium, cesium, calcium, magnesium, zinc or ammonium salts or mixtures thereof. In one embodiment, the vinyl monomers comprise pendant sulphonic acid groups, and/or carboxylic acid groups.

Conventional cross-linking agents (i.e., compounds which covalently-bond polymer chains together) are suitably used to provide the necessary mechanical stability and optionally to control the adhesive properties of the hydrogel. The amount of cross-linking agent required will be readily apparent to those skilled in the art such as from about 0.01, 0.05, or even 0.08% to about 0.5, 0.4, or even 0.3% by weight of the total polymerization reaction mixture. Typical cross-linkers comprise at least two polymerizable double bonds, and include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide. In one embodiment, the composition is substantially free (i.e., less than 0.001, or even 0.01 wt %) of conventional cross-linking agents as in known in the art and disclosed, for example, in Haraguchi et al. in Macromolecules v. 36 (2003) p. 5732-5741.

The hydrophilic monomers in the present invention are preferably interactive with the water-swellable clay, when polymerized. Preferably, some of the hydrophilic monomers have functional groups which can form hydrogen bonds, ionic bonds, and coordinate bonds, and covalent bonds with the water-swellable clay. Examples of such functional groups include an amide group, an amino group, a hydroxy group, a tetramethyl ammonium group, a silanol group, and an epoxy group.

The hydrophilic polymers used in this invention may have particular functions such that their polymer characteristics such as their hydrophilic properties or hydrophobic properties change remarkably as a result of a small temperature change, such as passing through the LCST (Lower Critical Solution Temperature).

Clay is typically added to a hydrogel composition to enhance the mechanical properties in the composites comprising large amounts of water. The water-swellable clay of the present disclosure, is a clay mineral capable of swelling and uniformly dispersing in water or a mixed solvent of water and an organic solvent. In one embodiment, the water-swellable clay is an inorganic clay mineral capable of uniformly dispersing in a molecular form (single layer) or level close thereto in water. More specifically, the water-swellable clay may contain sodium as an interlayer ion. Exemplary water-swellable clays include: synthetic hectorite $[Na_{0.3}(Mg,Li)_3Si_4O_{10}(OH)_2]$, saponite $[Ca_{0.25}(Mg,Fe)_3((Si,Al)_4O_{10})(OH)_2.n(H_2O)]$, montmorillonite $[(Na,Ca)_{0.33}(Al,Mg)_2(Si_4O_{10})(OH)_2.nH_2O]$, laponite $[Na^{+0.07}[(Si_3Mg_{5.5}Li_{0.3})O_{20}(OH)_4]^{-0.07}]$, monitrite, and synthetic mica.

The aqueous compositions of the present disclosure comprise at least 0.1% wt of the water-swellable clay versus the total weight of the aqueous composition. In one embodiment, the amount of water-swellable clay in the aqueous composition is at least 0.3, 0.5, or even 1 wt %; and at most 10, 15, or even 20 wt % versus the total weight of the aqueous composition.

The aqueous composition of the present disclosure comprises at least two different initiators: a first initiator, which is a Type I photoinitiator; and a second initiator, which is a Type II photoinitiator.

Photoinitiators for radical polymerization are classified in the art as cleavage (Type I) and hydrogen-abstraction (Type II) initiators. A Type I initiator, upon absorption of light, spontaneously undergoes "α-cleavage", yielding the initiating radical immediately. A Type II initiator is a photoinitiator which, when activated by actinic radiation, forms free radicals by hydrogen abstraction from a second (H-donor) compound to generate the actual initiating free radical. This second compound is called a polymerization synergist or co-initiator.

Type I and Type II photoinitiators are known in the art. These photoinitiators may not however, have sufficient water solubility to be used in the aqueous hydrogel compositions of the present disclosure. To improve the solubility of the photoinitiator, as is known in the art, the photoinitiator can be derivatized with a (more) hydrophilic group, the counter ion can be adjusted to improve the compound's water solubility, and/or a co-solvent can be used to aid the dissolution of the photoinitiator in the aqueous composition.

Examples of Type I photoinitiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Exemplary water-soluble Type I photoinitiators include: 4-[2-(4-morpholino)benzoyl-2-dimethylamino]-butylbenzenesulfonate salt, and phenyl-2,4,6-trimethylbenzoylphosphinate salt. Suitable salts include, for example, sodium and lithium cations. A commercial example of suitable water-soluble Type I photoinitiator is available from BASF SE, Ludwigshafen, Germany, under the trade designation: "IRGACURE 2959" (2-hydroxy-4'-(2-hydroxyethoxy)-2-methyl propiophenone).

Examples of Type II photoinitiators are modified benzophenones, benzils, and thioxanthones.

Exemplary Type II photoinitiators include those of the structure:

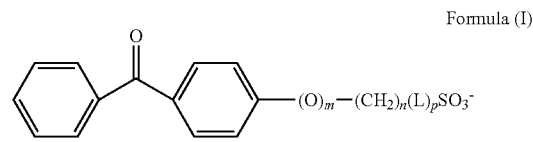

Formula (I)

where m is 0 or 1; n is 1, 2, 3, or 4; p is 0 or 1; and L is an alkylene group comprising from 1 to 4 carbons and having a hydroxyl group. In one embodiment, L is —CH(OH)CH$_2$—. Exemplary photoinitiators of Formula (I) include:

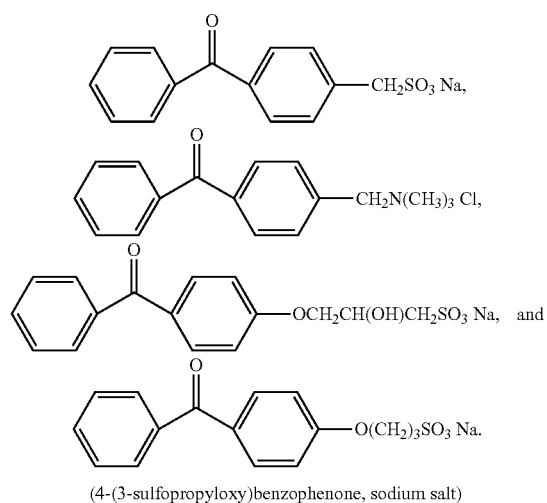

(4-(3-sulfopropyloxy)benzophenone, sodium salt)

Examples of Type II photoinitiators include those of the structure:

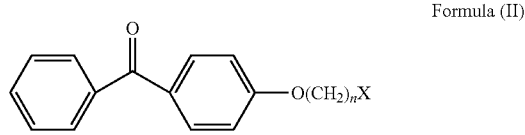

Formula (II)

where n is 1, 2, 3, or 4; and X is selected from —N(CH$_3$)$_3$SO$_3$CH$_3$, —CH(OH)—(CH$_2$)$_p$—N(CH$_3$)$_3$Cl where p is 1, 2, 3, or 4. Exemplary photoinitiators of Formula (II) include:

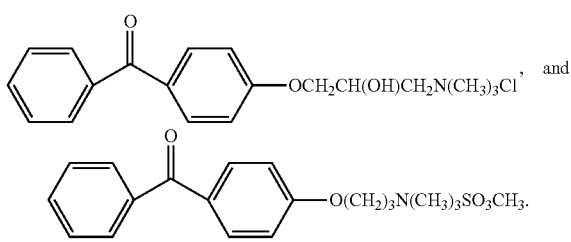

Examples of Type II photoinitiators include those of the structure:

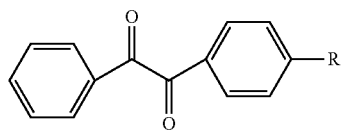

Formula (III)

Wherein R is -alkyl sulfonate comprising 1, 2, 3, or 4 carbon atoms (e.g., CH$_2$SO$_3$Na) or a tertiary amine salt comprising at 3, 4, 5, 6, or even 7 carbon atoms (e.g., —CH$_2$N(CH$_3$)$_3$Cl).

Examples of Type II photoinitiators include those of the structure:

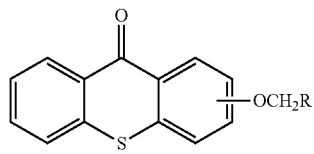

Formula (IV)

wherein R comprises a carboxylic acid or a tertiary amine and salts thereof. Exemplary R groups include —COOH, or —CH(OH)CH$_2$N(CH$_3$)$_3$Cl.

Exemplary water-soluble Type II photoinitiators include: 4-(3-sulfopropyloxy)benzophenone and 2-(3-sulfopropyloxy) thioxanthene-9-one, and 2-, 3-, and 4-carboxybenzophenone.

In the present disclosure, the at least one Type I and the at least one Type II photoinitiators are both water-soluble, which means that at ambient conditions (e.g., 23° C.), the photoinitiator has a solubility of at least 0.01, 0.1, 0.25, 0.5, 1, 2, 5 or even 8% by weight in water. If the solubility of the photoinitiator in water is too low, the photoinitiator will not be available for radical generation.

It has been discovered that both a Type I and a Type II photoinitiator are needed to create the durable attachment of a hydrogel onto a polymeric substrate of the present disclosure.

In one embodiment, the aqueous composition comprises at least 0.01, 0.05, 0.1, or even 0.5 wt %; and at most 1, 2, 4, or even 5 wt % of the first initiator, Type I based on the total weight of the aqueous composition.

In one embodiment, the aqueous composition comprises at least 0.01, 0.05, 0.1, 0.2, or even 0.5 wt %; and at most 1, 2, 4, or even 5 wt % of the second initiator, Type II based on the total weight of the aqueous composition.

Typically the weight ratio Type I photoinitiator:Type II photoinitiator is between 10:1 and 1:10, preferably between 5:1 and 1:5.

It has been discovered that by adjusting the pH of the aqueous composition, a durable hydrogel coating onto a polymeric substrate can be realized. In one embodiment, the addition of clay, monomers (or impurities therein), and/or additives (or impurities therein) employed can increase the pH of the coating composition. For example, as shown in the Example Section, the addition of the Laponite clay appears to increase the pH of the coating composition. As can be seen in the Examples of the present disclosure, when the pH of the coating composition is less than 9.5, 9, 8, 7, 6, or even 5, a durable attachment of the hydrogel to the polymeric substrate is achieved. Thus, an acid is added to the coating composition to adjust the pH to lower pH (i.e., more acidic) conditions to improve the bonding of the hydrogel onto the polymeric substrate.

Acids used to adjust the pH of the coating composition include those known in the art. Exemplary acids include: hydrochloric, perchloric, sulfuric, nitric, chloric, phosphoric, acetic, citric, acrylic, butyric, etc. The amount of acid used will vary depending on the strength (e.g., pKa) of the acid, the buffering capacity of the composition, and the pH of the hydrogel coating composition prior to the addition of the acid. For example, a strong acid (e.g., an acid that is completely dissociated in aqueous solution) may require a small amount to be used, while a weaker acid would require a larger amount to achieve the same pH value. For example, if the composition has a high buffering capacity, a greater amount of acid would be needed to change the pH.

The aqueous composition of the present invention may include one or more additional ingredients, which may be added prior to the curing (i.e., polymerization, grafting, and/or crosslinking) of the aqueous composition or after curing to impact the aesthetics and/or performance of the resulting hydrogel coating. It is generally preferred that substantially all of the final ingredients of the hydrogel are present in the aqueous composition, and that—apart from minor conventional conditioning or, in some cases, subsequent modifications caused by the sterilization procedure—substantially no chemical modification of the hydrogel takes place after completion of the polymerization reaction.

Such additional ingredients are selected from additives known in the art, including, for example, water, organic plasticizers, surfactants, polymeric material (hydrophobic or hydrophilic in nature, including proteins, enzymes, naturally occurring polymers and gums), synthetic polymers with and without pendant carboxylic acids, electrolytes, osmolytes, pH regulators, colorants, chloride sources, bioactive compounds and mixtures thereof. In some embodiments, the additional ingredients may serve more than one purpose. For example, glycerol may serve as an organic plasticizer and an osmolyte.

In one embodiment, an additional polymer may be added. The polymer can be a natural polymer (e.g. xanthan gum), synthetic polymer (e.g. polyoxypropylene-polyoxyethylene block copolymer or poly-(methyl vinyl ether alt maleic anhydride)), or any combination thereof. In one embodiment, a rheology modifying polymer may be incorporated into the aqueous composition at levels typically up to about 10% by weight of total polymerization reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

In one embodiment, a bioactive compound may be added. The term "bioactive compounds" is used to mean any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. The hydrogel may incorporate antimicrobial agents, for example, those active against such organisms as *Staphylococcus aureus* and *Pseudomonas aeruginosa*. Antimicrobial agents may, for example, include: sources of oxygen and/or iodine (e.g. hydrogen peroxide or a source thereof and/or an iodide salt such as potassium iodide); antimicrobial metals, metal ions and salts, such as, for example, silver-containing antimicrobial agents (e.g. colloidal silver, silver oxide, silver nitrate, silver thiosulphate, silver sulphadiazine, or any combination thereof), hypochlorous acid; or any combination thereof.

In one embodiment, agents for stimulating the healing of wounds and/or for restricting or preventing scarring may be incorporated into the hydrogel. Examples of such agents include growth factors such as TGF (transforming growth factor), PDGF (platelet derived growth factor), KGF (keratinocyte growth factor, e.g. KGF-I or KGF-2), VEGF (vascular endothelial growth factor), IGF (insulin growth factor, optionally in association with one or more of IGF binding protein and vitronectin); cell nutrients; glucose; an anabolic hormone or hormone mixture such as insulin, triiodothyronine, thyroxine or any combination thereof; or any combination thereof.

In one embodiment, the aqueous composition further comprises a humectant such as polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums. The amount of humectant added can vary based on the type used. For example typically no more than 30%, 40%, 50% or even 60% by wt of glycerol can be added.

In one embodiment, one or more plasticizers, preferably one or more organic plasticizer is added. The one or more organic plasticizer, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticizer. An alternative preferred plasticizer is the ester derived from boric acid and glycerol. When present, the organic plasticizer may comprise up to about 45%, for example up to about 35%, for example up to about 25%, for example up to about 15%, by weight of the hydrogel composition.

In one embodiment, the aqueous composition comprises a compatible surfactant. Surfactants can lower the surface tension of the mixture before polymerization and thus aid processing. The surfactant or surfactants may be non-ionic, anionic, zwitterionic or cationic, alone or in any mixture or combination. The surfactant may itself be reactive, i.e. capable of participating in the hydrogel-forming reaction. The total amount of surfactant, if present, is suitably up to about 10% by weight of the aqueous composition, preferably from about 0.05% to about 4% by weight. The surfactant may, for example, comprise at least one propylene oxide/ethylene oxide block copolymer, for example such as that supplied by BASF PLC under the trade name Pluronic P65 or L64.

Additional osmolyte(s) may be included to modify the osmolality of the hydrogel. Osmolytes may be ionic (e.g. electrolytes, for example salts which are readily soluble in the aqueous phase of the hydrogel to increase the ionic strength of selected cations or anions and hence the osmolality of the hydrogel). By selecting the ions present in an ionic osmolyte, and particularly by selecting the cation so as to correspond or not with cationic counterions in the monomer(s) of the hydrogel, the ionic strength of certain anions (e.g. chloride) can be varied with fine control, without substantially changing the ionic strength of cations already present in very large amounts as counterions of the monomer(s). Osmolytes may be organic (non-ionic), for example organic molecules which dissolve in or intimately mix with the aqueous phase of the hydrogel to increase the osmolality of the hydrogel deriving from non-ionic species in the aqueous phase. Such organic osmolytes include, for example, water-soluble sugars (e.g. glucose, fructose and other monosaccharides; sucrose, lactose, maltose and other disaccharides; or any combination of mono- and di-saccharides), polyhydric alcohols (e.g. glycerol and other polyhydroxylated alkanols).

In addition to water, in one embodiment an water miscible organic solvent may be used. Examples of such organic solvents include methanol, acetone, methyl ethyl ketone and tetrahydrofuran. The mixing ratio of water to the organic solvent can be optionally selected within a range wherein the water swelling clay can be homogeneously dispersed.

In one embodiment, the aqueous composition is substantially free of water miscible solvent, in other words, the aqueous composition comprises less than 5%, 1% or even 0.5% organic solvent versus the weight of the aqueous composition.

The aqueous composition may be prepared using techniques known in the art. Briefly, the monomers, clay, water, initiators and any additional components may be added together.

The hydrogel may be formed in situ on the polymeric substrate. Additional layers may be added to the hydrogel coating and polymeric substrate construction to form desired articles, such as a wound dressing.

The aqueous composition containing the monomer(s) and preferably cross-linking agent, water, photoinitiators, and optionally other additional ingredients, is initially laid down on the polymeric substrate. Where the hydrogel composition is to be prepared in sheet form, the polymeric substrate will be a sheet. It may suitably comprise the backing layer or a release layer and any desired sheet support member that may be interposed between the release layer and the hydrogel composition, or embedded within the hydrogel composition, in the finished dressing. In this way, the aqueous composition can be polymerized in situ on the release layer, preferably with all or substantially all other components of the final dressing in place.

The aqueous composition can be coated onto the polymeric substrate using techniques known in the art. Exemplary coating methods include knife coating, bar coating, gravure coating, spray coating, etc.

In one embodiment, the polymeric substrate may be cleaned or treated prior to contact with the aqueous composition. Such methods are known in the art and include: solvent cleaning, plasma treatment, corona treatment, etc.

In the present disclosure, the polymeric substrate is substantially free of a primer layer. As disclosed herein a primer is a substance, either liquid or solid, applied to a substrate in order to increase the adhesion of the hydrogel to the substrate. Such primers include: a tie layer or adhesive layer.

The coating composition of the present disclosure can be cured using actinic radiation, including for example, visible light or UV. Of these, ultraviolet rays is preferred in light of apparatus simplicity and handling convenience. The irradiation intensity of ultraviolet rays is preferably 1 to 500 mW/cm$^2$ and an irradiation period is generally 0.1 to 2000 seconds Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing. UV radiation is generally classed as UV-A, UV-B, and UV-C as follows: UV-A: 400 nm to 320 nm; UV-B: 320 nm to 290 nm; and UV-C: 290 nm to 100 nm.

Thickness of the resulting coating layer can vary depending on the application. For example, in in vivo applications (e.g., stents), the thickness of the coating layer can range from at least 10 nm or even 100 nm to at most 1 μm, 10 μm, or even 100 μm. For example, in wound care applications, the thickness of the coating layer can range from at least 0.1 mm, 0.25 mm or even 0.5 mm to at most 2 mm, 3 mm, or even 10 mm.

After completion of the polymerization, the product is preferably sterilized in conventional manner. The sterile composite may be used immediately, e.g. to provide a skin-adhesive layer in an article, or a top release layer may be applied to the composite for storage and transportation of the composite.

In one embodiment, the multilayer articles of the present disclosure are transparent.

The water content absorbed by the resulting hydrogel can be a function of the monomers used, for example HEMA and vinyl pyrrolidone and glycerol methacrylate and acrylamide monomers have been used form hydrogels with high water content. Acid-containing monomers such as (meth)acrylic acid and 2-acrylamido-2-methylpropanesulfonic acid provide ionic character at pH above 4 and contribute to large amounts of water absorption.

The hydrogel sheet may be part of a multi-layer composite, including further layers such as further hydrogels and/or other polymers and/or other sheet support members. For example, a breathable (air and/or moisture permeable) polymeric film (e.g. of polyurethane), which may if desired be present as a foam, may overlie the hydrogel sheet or composite on the major face of the sheet or composite directed away from the lesion in use. The breathable polymeric film may be, or may constitute part of, the backing layer.

The hydrogel composition and other sheet components as desired may preferably be provided with a release layer (e.g. of non-stick paper or plastic, such as siliconized paper or plastic) to protect one or both major face of the sheet prior to use.

Because of their high water content, hydrogels are often inherently biocompatible. Thus, these articles may be used in wound dressings or in devices/articles meant for contact with biological tissues.

A non-limiting list of exemplary embodiments and combinations of exemplary embodiments of the present disclosure are disclosed below.

Embodiment 1

A multilayer article comprising:
(i) a polymeric substrate comprising an abstractable atom; and
(ii) a hydrogel coating thereon wherein the hydrogel coating has a water content of at least 10 wt % and is covalently bonded to the polymer substrate, and wherein the hydrogel coating is derived from an aqueous composition having a pH less than 9.5, the aqueous composition comprising:
(a) a hydrophilic monomer selected from at least one of (meth)acrylate or (meth)acrylamide;
(b) at least 0.1 wt % of a water-swellable clay;
(c) a first initiator, wherein the first initiator is water-soluble and is a Type I photoinitiator; and
(d) a second initiator, wherein the initiator is water-soluble and is a Type II photoinitiator; and
(e) an acid.

Embodiment 2

The multilayer article of embodiment 1, wherein the polymer substrate comprises at least one of polyurethanes, polyamide, polyester, and polypropylene.

Embodiment 3

The multilayer article of any one of the previous embodiments, wherein the polymer substrate is substantially free of a primer.

Embodiment 4

The multilayer article of any one of the previous embodiments, wherein the first initiator is selected from at least one of: 2-hydroxy-4'-(2-hydroxyethoxy)-2-methyl propiophenone.

Embodiment 5

The multilayer article of any one of the previous embodiments, wherein the second initiator comprises at least one of: 4-(3-sulfopropyloxy)benzophenone, 2-(3-sulfopropyloxy)thioxanthen-9-one, carboxybenzophenone, and salts thereof.

Embodiment 6

The multilayer article of any one of the previous embodiments, wherein the aqueous composition is substantially free of an alcohol.

Embodiment 7

The multilayer article of any one of the previous embodiments, wherein the aqueous composition comprises 0.5-20% by weight of the water-swellable clay.

Embodiment 8

The multilayer article of any one of the previous embodiments, wherein the aqueous composition comprises 0.001 to 5% by weight of the first initiator.

Embodiment 9

The multilayer article of any one of the previous embodiments, wherein the aqueous composition comprises 0.01 to 5% by weight of the second initiator.

Embodiment 10

The multilayer article of any one of the previous embodiments, wherein the aqueous composition has a pH less than 8.

Embodiment 11

The multilayer article of any one of the previous embodiments, wherein the hydrogel coating has a thickness of at least 0.1 mm.

Embodiment 12

The multilayer article of any one of the previous embodiments, wherein the water-swellable clay is selected from at least one of laponite, synthetic hectorite, and montmorillonite.

Embodiment 13

The multilayer article of any one of the previous embodiments, wherein the hydrogel coating further comprises an additive selected from at least one of polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, and natural gums.

Embodiment 14

The multilayer article of any one of the previous embodiments, wherein the hydrogel coating further comprises an antimicrobial agent.

Embodiment 15

The multilayer article of any one of the previous embodiments, wherein the multilayer article is a wound dressing.

Embodiment 16

A method of making a hydrogel coated article, the method comprising:
(i) providing an aqueous composition having a pH less than 9.5, the aqueous composition comprising:
  (a) a hydrophilic monomer selected from at least one of (meth)acrylate or (meth)acrylamide;
  (b) at least 0.1 wt/wt % of a water-swellable clay;
  (c) a first initiator, wherein the initiator is water-soluble and is a Type I photoinitiator;
  (d) a second initiator, wherein the initiator is water-soluble and is a Type II photoinitiator; and
  (e) an acid;
(ii) contacting the aqueous composition to a polymer substrate comprising an abstractable atom; and
(iii) curing the aqueous composition.

Embodiment 17

The method of embodiment 16, wherein the curing is by UV radiation.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used herein: g=grams, rpm=revolutions per minute, min=minutes, ° C.=degrees Celsius, wt=weight, and mW=milliWatt.

Materials:

Reagent grade N,N-dimethylacrylamide (DMA) and Ultrapure methylenebisacrylamide (MBA) were purchased from Sigma-Aldrich (St. Louis, Mo.). Photoinitiator 1, 1-[4-(2-Hydroxyethoxy)-phenyl]-2-hydroxy-2-methyl-1-propane-1-one available under the trade designation "CIBA IRGACURE 2959" was purchased from BASF (Florham Park, N.J.). Salts and solid acids were purchased from Alfa Aesar (Ward Hill, Mass.). The 4-(3-sulfopropyloxy)benzophenone, sodium salt (BzS), was prepared essentially as described in Japanese Patent No. 47040913, Teijin Ltd. All Laponite clay materials were obtained from Rockwood Additives (BYK Additives Inc, Gonzales, Tex.). Unless otherwise noted, all aqueous compositions were prepared with 18 MΩ water from a water purification system (available under the trade designation "Milli-Q" from EMD Millipore, Billerica, Mass.). Stock solutions were prepared with water at the following wt %: 2% MBA, 5% BzS, 10% tripotassium citrate ($K_3$ Citrate), 10% Citric Acid, 10% Acetic Acid, and 10% Sodium Chloride (NaCl). 1N HCl was used as is from J.T. Baker (Center Valley, Pa.).

Testing:

pH: An Orion 3 Star pH Meter equipped with an 8157 BNC Ross Ultra pH/ATC Triode electrode (Thermo Scientific, Waltham, Mass.) was used to measure pH. The pH meter was calibrated using a 3 point calibration that followed the vendor-provided procedure and calibration standards at pH 4, 7, and 10 (BDH, Dubai, UAE).

Qualitative Adhesion: The adhesion of the cured hydrogel layer to the polyurethane substrate was determined as follows: Test 1: The cured multilayer article was inverted such that the cured hydrogel faced downward with the polyurethane substrate facing upward. If the hydrogel detached from the polyurethane substrate a "3" rating was given. Test 2: If the multilayer article passed Test 1, then, the hydrogel coating layer on the cured multilayer article was compressed between the tester's thumb and index finger. If the hydrogel coating detached from the polyurethane substrate a "2" rating was given. If the multilayer article passed both tests, a "1" rating was given.

Preparation of Examples 1-8: A 125 mL glass jar was charged with water and equipped with a polytetrafluoroethylene-coated stir bar. While stirring with a magnetic stir plate at 450 rpms, Laponite XLG clay was added. The composition was allowed to mix for 15 minutes, by which time it became clear and colorless. Next, while stirring DMA, Photoinitiator 1, an aliquot of a 2% MBA solution, and an aliquot of a 5% BzS solution, were added. After stirring for an additional 15 minutes, an acid (Citric acid, Acetic acid, HCl, or Acrylic acid) was added to the composition. The composition was mixed for an additional 5 minutes, and then the pH of the coating composition was measured. The amounts used in grams are listed in Table 1 below for Examples 1-8 (Ex. 1-Ex. 8).

The coating composition was coated at a thickness of 1.5 mm onto a polyurethane film (available under the trade designation "3M POLYURETHANE TAPE 9832F ON WHITE CARRIER" 0.8 mil (20 µm), from 3M Co., St. Paul, Minn.) and a polyethylene terephthalate release liner coated with silicone release coating was placed on top of the coating composition with the silicone release coating facing toward the coating composition. The construction (i.e., polyurethane/coating composition/PET release liner) was then exposed to UV light through the PET release liner for 20 minutes using 40 Watt Sylvania black lights (350 nm) such that the irradiance was 4 mW/cm$^2$ and then the PET release liner was removed resulting in a hydrogel coating on a polyurethane substrate.

TABLE 1

| Components | Ex. 1 | Ex. 2 | Ex. 3 | Ex. 4 | Ex. 5 | Ex. 6 | Ex. 7 | Ex. 8 |
|---|---|---|---|---|---|---|---|---|
| Water | 81.8 | 83.1 | 82.7 | 83.0 | 83.3 | 43.595 | 37.595 | 50.17 |
| XLG Clay | 3.0 | 3.0 | 3.0 | 3.0 | 3.0 | 1.8 | 1.8 | 1.8 |
| DMA | 9.95 | 9.95 | 9.95 | 9.95 | 9.95 | 12.0 | 18.0 | 6.0 |
| Photoinitiator 1 | 0.050 | 0.050 | 0.050 | 0.050 | 0.050 | 0.030 | 0.030 | 0.030 |
| 2% MBA | 1.25 | 1.25 | 1.25 | 1.25 | 1.25 | 0.750 | 0.750 | 0.75 |
| 5% BzS | 2.0 | 2.0 | 2.0 | 2.0 | 2.0 | 1.20 | 1.20 | 1.20 |
| 10% Citric Acid | 1.997 | — | — | — | — | — | — | — |
| 10% Acetic Acid | — | 0.608 | — | — | — | — | — | — |
| 1N HCl | — | — | 1.042 | 0.751 | 0.501 | 0.625 | 0.625 | — |
| Acrylic Acid | — | — | — | — | — | — | — | 0.05 |

Preparation of Examples 9-14: A 125 mL glass jar was charged with water and equipped with a polytetrafluoroethylene-coated stir bar. While stirring with a magnetic stir plate at 450 rpms, 1.80 g of Laponite XLG clay was added. The composition was allowed to mix for 15 minutes, by which time it became clear and colorless. Next, while stirring, 6.0 g of DMA, 0.03 g of Photoinitiator 1, 0.750 g of a 2% solution of MBA, an aliquot of a 5% solution of BzS, and glycerol, if noted, were added. After stirring for an additional 15 minutes, an aliquot of 1N HCl was added to the composition. The composition was mixed for an additional 5 minutes, and then the pH was measured. The amounts used in grams are listed in Table 2 below for Examples 9-14 (Ex. 9-Ex. 14).

The coating composition was coated at a thickness of 1.5 mm onto a polyurethane film (available under the trade designation "3M POLYURETHANE TAPE 9832F ON WHITE CARRIER" 0.8 mil (20 μm), from 3M Co., St. Paul, Minn.) and a polyethylene terephthalate release liner coated with silicone release coating was placed on top of the coating composition with the silicone release coating facing toward the coating composition. The construction (i.e., polyurethane/coating composition/PET release liner) was then exposed to UV light through the PET release liner for 20 minutes using 40 Watt Sylvania black lights (350 nm) such that the irradiance was 4 mW/cm$^2$ and then the PET release liner was removed resulting in a hydrogel coating on a polyurethane substrate.

TABLE 2

| Component | Ex. 9 | Ex. 10 | Ex. 11 | Ex. 12 | Ex. 13 | Ex. 14 |
|---|---|---|---|---|---|---|
| Water | 43.595 | 37.595 | 31.595 | 50.19 | 50.49 | 50.67 |
| 5% BzS | 1.20 | 1.20 | 1.20 | 0.60 | 0.30 | 0.12 |
| 1N HCl | 0.625 | 0.625 | 0.625 | 0.625 | 0.625 | 0.625 |
| Glycerol | 6.0 | 12.0 | 18.0 | — | — | — |

Preparation of Comparative Examples: A 125 mL glass jar was charged with water and equipped with a polytetrafluoroethylene-coated stir bar. While stirring with a magnetic stir plate at 450 rpms, Laponite XLG clay was added. The composition was allowed to mix for 15 minutes, by which time it became clear and colorless. Next, while stirring, DMA, Photoinitiator 1 (if noted), an aliquot of a 2% solution of MBA, and an aliquot of a 5% solution of BzS (if noted) were added. After stirring for an additional 15 minutes, an acid or salt solution (K$_3$ Citrate, citric acid, acetic acid, HCl, or NaCl) was added to the composition. The composition then was mixed for an additional 5 minutes, and then the pH was measured. The amounts used are listed in Table 3 below for Comparative Examples 1-6 (CE 1-CE 6).

The coating composition was coated at a thickness of 1.5 mm onto a polyurethane film (available under the trade designation "3M POLYURETHANE TAPE 9832F ON WHITE CARRIER" 0.8 mil (20 μm), from 3M Co., St. Paul, Minn.) and a polyethylene terephthalate release liner coated with silicone release coating was placed on top of the coating composition with the silicone release coating facing toward the coating composition. The construction (i.e., polyurethane/coating composition/PET release liner) was then exposed to UV light through the PET release liner for 20 minutes using 40 Watt Sylvania black lights (350 nm) such that the irradiance was 4 mW/cm$^2$ and then the PET release liner was removed resulting in a hydrogel coating on a polyurethane substrate.

TABLE 3

| Material | CE 1 | CE 2 | CE 3 | CE 4 | CE 5 | CE 6 |
|---|---|---|---|---|---|---|
| Water | 80.4 | 85.0 | 83.6 | 83.0 | 49.6 | 83.7 |
| XLG Clay | 3 | 3 | 3 | 3 | 1.8 | 3.0 |
| DMA | 9.95 | 9.95 | 9.95 | 9.95 | 6 | 9.95 |
| 2% MBA | 1.25 | 1.25 | 1.25 | 1.25 | 0.75 | 0.050 |
| Photoinitiator 1 | 0.05 | 0.05 | 0.05 | 0.05 | — | 1.25 |
| 5% BzS | 2.0 | — | 2.0 | 2.0 | 1.2 | 2.00 |
| 10% K$_3$ Citrate | 3.37 | — | — | — | — | — |
| 10% Acetic Acid | — | — | — | — | — | 0.100 |
| 1N HCl | — | 1.042 | — | — | 0.625 | — |
| 10% NaCl | — | — | — | 0.608 | — | — |

Shown in Table 4 is a summary of the acid or salt used, if any, amount of the Type II initiator used (BzS), the pH of the hydrogel coating composition before curing, and the relative adhesion observed for the cured hydrogel on the substrate.

TABLE 4

| Sample | Acid or Salt Used | Wt % BzS | pH | Qualitative Adhesion |
|---|---|---|---|---|
| 1 | Citric Acid | 0.1 | 5.85 | 1 |
| 2 | Acetic Acid | 0.1 | 7.52 | 1 |
| 3 | HCl | 0.1 | 7.18 | 1 |
| 4 | HCl | 0.1 | 8.34 | 1 |
| 5 | HCl | 0.1 | 9.04 | 2 |
| 6 | HCl | 0.1 | 7.19 | 1 |
| 7 | HCl | 0.1 | 7.21 | 1 |

TABLE 4-continued

| Sample | Acid or Salt Used | Wt % BzS | pH | Qualitative Adhesion |
|---|---|---|---|---|
| 8 | Acrylic Acid | 0.1 | 6.33 | 1 |
| 9 | HCl | 0.1 | 7.05 | 1 |
| 10 | HCl | 0.1 | 6.91 | 2 |
| 11 | HCl | 0.1 | 6.88 | 2 |
| 12 | HCl | 0.05 | 7.03 | 1 |
| 13 | HCl | 0.025 | 7.08 | 2 |
| 14 | HCl | 0.01 | 7.10 | 2 |
| CE 1 | K3 Citrate | 0.1 | 10.16 | 3 |
| CE 2 | HCl | — | 7.50 | 3 |
| CE 3 | — | 0.1 | 10.23 | 3 |
| CE 4 | NaCl | 0.1 | 10.16 | 3 |
| CE 5* | HCl | 0.1 | 7.17 | 3 |
| CE 6 | HCl | 0.1 | 10.09 | 3 |

*No Photoinitiator 1 was used.

Comparative Example 7

Various amounts of Laponite XLG clay were added to water and stirred. The pH of the resulting mixture was determined after 30 minutes. The results are shown in Table 5 below.

TABLE 5

| Sample | Water (g) | Clay (g) | % Clay | pH |
|---|---|---|---|---|
| A | 59.94 | 0.06 | 0.10% | 9.94 |
| B | 59.7 | 0.3 | 0.5% | 10.18 |
| C | 59.4 | 0.6 | 1% | 10.18 |
| D | 58.8 | 1.2 | 2% | 10.13 |
| E | 58.2 | 1.8 | 3% | 10.12 |
| F | 57.6 | 2.4 | 4% | 10.14 |

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A multilayer article comprising:
   a polymeric substrate comprising an abstractable atom; and
   (ii) a hydrogel coating thereon wherein the hydrogel coating has a water content of at least 10 wt % and is covalently bonded to the polymer substrate, and wherein the hydrogel coating is derived from an aqueous composition having a pH less than 9.5, the aqueous composition comprising:
   (a) a hydrophilic monomer selected from at least one of (meth)acrylate or (meth)acrylamide;
   (b) at least 0.1 wt % of a water-swellable clay;
   (c) a first initiator, wherein the first initiator is water-soluble and is a Type I photoinitiator; and
   (d) a second initiator, wherein the second initiator is water-soluble and is a Type II photoinitiator; and
   (e) an acid, wherein the polymer substrate is substantially free of a primer.

2. The multilayer article of claim 1, wherein the polymer substrate is selected from the group consisting of polyurethanes, polyester, polypropylene, and combinations thereof.

3. The multilayer article of claim 1, wherein the first initiator is 2-hydroxy-4'-(2-hydroxyethoxy)-2-methyl propiophenone.

4. The multilayer article of claim 1, wherein the aqueous composition is substantially free of an alcohol.

5. The multilayer article of claim 1, wherein the aqueous composition has a pH less than 8.

6. The multilayer article of claim 1, wherein the hydrogel coating has a thickness of at least 0.1 mm.

7. The multilayer article of claim 1, wherein the hydrogel coating further comprises an additive selected from the group consisting of polyethylene glycol, polyethylene glycol-co-polypropylene oxide copolymers, partially hydrolyzed polyvinyl acetate, polyvinyl pyrrolidone, glycerol or glycerol derivative, methylcellulose or other cellulose derivative, polyoxazoline, natural gums, and combinations thereof.

8. The multilayer article of claim 1, wherein the multilayer article is a wound dressing.

9. The multilayer article of claim 1, wherein the second initiator is selected from the group consisting of 4-(3-sulfopropyloxy)benzophenone, 2-(3-sulfopropyloxy) thioxanthen-9-one, carboxybenzophenone, salts thereof, and combinations thereof.

10. The multilayer article of claim 1, wherein the aqueous composition comprises 0.5-20% by weight of the water-swellable clay.

11. The multilayer article of claim 1, wherein the aqueous composition comprises 0.001 to 5% by weight of the first initiator.

12. The multilayer article of claim 1, wherein the aqueous composition comprises 0.01 to 5% by weight of the second initiator.

13. The multilayer article of claim 1, wherein the water-swellable clay is selected from the group consisting of laponite, synthetic hectorite, montmorillonite, and combinations thereof.

14. The multilayer article of claim 1, wherein the hydrogel coating further comprises an antimicrobial agent.

15. The multilayer article of claim 1, wherein the polymer substrate comprises a polyurethane.

16. The multilayer article of claim 1, wherein the polymer substrate is a polyurethane.

17. The multilayer article of claim 1, further comprising a release liner on the hydrogel coating.

18. A method of making a hydrogel coated article, the method comprising:
   (i) providing an aqueous composition having a pH less than 9.5, the aqueous composition comprising:
   (a) a hydrophilic monomer selected from at least one of (meth)acrylate or (meth)acrylamide;
   (b) at least 0.1 wt % of a water-swellable clay;
   (c) a first initiator, wherein the first initiator is water-soluble and is a Type I photoinitiator;
   (d) a second initiator, wherein the second initiator is water-soluble and is a Type II photoinitiator; and
   (e) an acid;
   (ii) contacting the aqueous composition to a polymer substrate comprising an abstractable atom, wherein the polymer substrate is substantially free of a primer; and
   (iii) curing the aqueous composition to provide a hydrogel coating on the polymer substrate, wherein the hydrogel coating has a water content of at least 10 wt % and is covalently bonded to the polymer substrate.

19. The method of claim 18, wherein the curing is by UV radiation.

* * * * *

UNITED STATES PATENT AND TRADEMARK OFFICE
CERTIFICATE OF CORRECTION

PATENT NO. : 11,638,775 B2
APPLICATION NO. : 15/753196
DATED : May 2, 2023
INVENTOR(S) : Alexi J Young Page 1 of 1

It is certified that error appears in the above-identified patent and that said Letters Patent is hereby corrected as shown below:

In the Claims

Column 17
Line 57-58 (approx.), In Claim 1, delete "polymer substrate is substantially free of" and insert
-- polymer substrate is free of --, therefor.

Column 18
Line 57, In Claim 18, "polymer substrate is substantially free of" and insert -- polymer substrate is free of --, therefor.

Signed and Sealed this
Sixth Day of February, 2024

Katherine Kelly Vidal
*Director of the United States Patent and Trademark Office*